United States Patent
Ueda et al.

(10) Patent No.: US 10,258,349 B2
(45) Date of Patent: Apr. 16, 2019

(54) ARTHROSCOPIC SURGERY METHOD FOR ANKLE IMPINGEMENT

(71) Applicant: OLYMPUS CORPORATION, Tokyo (JP)

(72) Inventors: Sohei Ueda, Tokyo (JP); Chie Onuma, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 370 days.

(21) Appl. No.: 15/085,391

(22) Filed: Mar. 30, 2016

(65) Prior Publication Data
US 2017/0172587 A1    Jun. 22, 2017

Related U.S. Application Data

(60) Provisional application No. 62/269,566, filed on Dec. 18, 2015.

(51) Int. Cl.
| | | |
|---|---|---|
| *A61B 17/16* | (2006.01) | |
| *A61B 17/32* | (2006.01) | |
| *A61B 17/3205* | (2006.01) | |
| *A61B 17/00* | (2006.01) | |
| *A61B 17/56* | (2006.01) | |

(52) U.S. Cl.
CPC .... *A61B 17/1682* (2013.01); *A61B 17/00234* (2013.01); *A61B 17/3205* (2013.01); *A61B 17/320068* (2013.01); *A61B 2017/564* (2013.01)

(58) Field of Classification Search
CPC ............... A61B 17/1659; A61B 17/56; A61B 17/320068; A61B 17/1682
See application file for complete search history.

(56) References Cited

U.S. PATENT DOCUMENTS

| | | | | |
|---|---|---|---|---|
| 5,871,486 A | * | 2/1999 | Huebner | A61B 17/1686 411/415 |
| 6,579,293 B1 | * | 6/2003 | Chandran | A61B 17/1725 606/62 |
| 7,981,158 B2 | * | 7/2011 | Fitz | A61B 5/4528 128/898 |
| 8,617,164 B2 | * | 12/2013 | Nelson | A61B 17/1624 606/171 |
| 9,005,203 B2 | * | 4/2015 | Nelson | A61B 17/1624 606/171 |
| 9,387,019 B2 | * | 7/2016 | Duggal | A61B 17/683 |
| 2004/0039394 A1 | * | 2/2004 | Conti | A61B 17/15 606/87 |
| 2005/0107791 A1 | * | 5/2005 | Manderson | A61B 17/68 606/62 |
| 2006/0020343 A1 | * | 1/2006 | Ek | A61B 17/1675 623/18.11 |

(Continued)

*Primary Examiner* — Zade Coley
(74) *Attorney, Agent, or Firm* — Oliff PLC

(57) ABSTRACT

An arthroscopic surgery method for ankle impingement of the embodiment removes a posterior process of talus from the portal formed in the position specified beforehand by vibrating ultrasonically of an ultrasonic treatment tool which inserted and inserted the ultrasonic treatment tool to the posterior process of talus and a tendon sheath of flexor hallucis longus muscle tendon, and deletes the tendon sheath of flexor hallucis longus muscle tendon by the ultrasonic treatment tool used for deleting the posterior process of talus.

8 Claims, 8 Drawing Sheets

(56) References Cited

U.S. PATENT DOCUMENTS

| | | | | |
|---|---|---|---|---|
| 2006/0095043 A1* | 5/2006 | Martz | ............... | A61B 17/1671 |
| | | | | 606/90 |
| 2007/0275348 A1* | 11/2007 | Lemon | ................. | A61C 3/03 |
| | | | | 433/119 |
| 2011/0166609 A1* | 7/2011 | Duggal | ............... | A61B 17/683 |
| | | | | 606/328 |
| 2011/0208256 A1* | 8/2011 | Zuhars | ............... | A61F 2/30756 |
| | | | | 606/86 R |
| 2012/0165701 A1* | 6/2012 | Manderson | ........ | A61B 17/7225 |
| | | | | 600/587 |

* cited by examiner

ARTHROSCOPIC SURGERY METHOD FOR ANKLE IMPINGEMENT

CROSS-REFERENCE TO RELATED APPLICATIONS

This application is based upon and claims the benefit of priority from the prior U.S. Provisional Application No. 62/269,566 filed Dec. 18, 2015, the entire contents of which are incorporated herein by reference.

BACKGROUND OF THE INVENTION

1. Field of the Invention

The present invention relates to an arthroscopic surgery method for ankle impingement using an ultrasonic treatment tool.

2. Description of the Related Art

In arthroscopic surgery, portals as small holes are generally made in a few locations around a joint (skin surface) and an arthroscope made of rigid mirrors, a treatment tool and the like are inserted from these portals. Then, surgery is performed while videos in a monitor being checked in a state in which the inside of joint is filled with a perfusion such as physiological saline.

In arthroscopic surgery using conventional treatment tools, there are causes for concern about some procedures. In a portal created frontward, there awe some cases in which the treatment tool cannot reach the site (portion) to be treated or some locations where treatment cannot be given because sufficient space for treatment is not available. Thus, it may become necessary to make a new hole. Also, the corresponding treatment tool is different depending on the treatment content and thus, a plurality of treatment tool is needed and also the frequency with which treatment tools are replaced during surgery is high.

A treatment tool that cuts in a plane direction using rotary blade cuts a bone by moving the rotary blade while rotating and thus, unevenness is left on the treatment surface and it is not easy to smooth the surface. Further, when a treatment tool using high frequencies is used, if thermal damage extending over surrounding tissues including the tissue to be treated is caused, it may take time before the postoperative conditions become good. Particularly, among joints, the ankle is expressly narrow and thus, unevenness is likely to be left and also thermal damage is likely to be done.

BRIEF SUMMARY OF THE INVENTION

According to an embodiment of the present invention, there is provided an arthroscopic surgery method for ankle impingement in an embodiment according to the present invention includes: inserting an ultrasonic treatment tool from at least two portals such that a tip of a probe of the ultrasonic treatment tool reaches a posterior process of talus and a tendon sheath of flexor hallucis longus muscle tendon to be treated; removing the posterior process of talus using the probe vibrating ultrasonically of the ultrasonic treatment tool inserted in the step of insertion; and shaving the tendon sheath of flexor hallucis longus muscle tendon using the probe vibrating ultrasonically of the ultrasonic treatment tool used in the step of removal.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Figure 1:
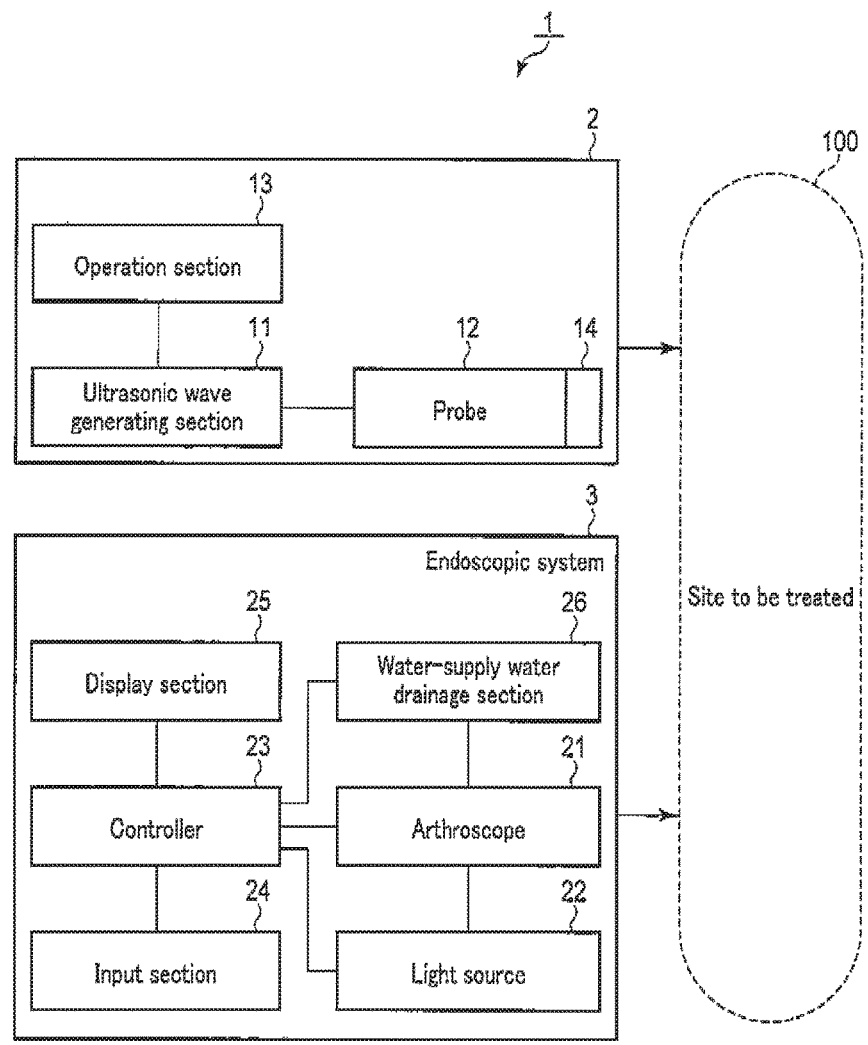
FIG. 1 is a diagram showing a configuration example of an operation system including an ultrasonic treatment tool to perform an arthroscopic method for ankle arthrodesis according to the present embodiment.

Hereinafter, an arthroscopic surgery method for ankle impingement using an ultrasonic treatment tool according to an embodiment of the present invention will be described with reference to the drawings. FIG. 1 shows a configuration example of an operation system including an ultrasonic treatment tool to perform an arthroscopic method for ankle arthrodesis according to the present embodiment.

An operation system 1 according to the present embodiment includes an ultrasonic treatment tool 2 and an endoscopic system 3 including an arthroscope 21.

The ultrasonic treatment tool 2 includes an ultrasonic wave generating section 11 that generates an ultrasonic vibration using an ultrasonic vibration element (for example, a piezoelectric element), an elongated probe 12 that carries out a cutting procedure of the site to be treated by transmitting the ultrasonic vibration, and an operation section 13 that performs an ON/OFF operation of the generation of an ultrasonic vibration. The probe 12 has a treatment section 14 provided at the tip thereof and the treatment section 14 performs a cutting procedure or a dissection procedure for, for example, living body tissues, cartilages, and bones (subchondral bones) using ultrasonic vibrations. The treatment section 14 can shave off the bone such as a subchondral bone by knocking (hammering) the bone like a hammer using ultrasonic vibrations to pulverize the bone into extremely fine pieces.

The endoscopic system 3 includes the arthroscope 21 constructed of a rigid mirror as a kind of an endoscope, a light source 22 that radiates an illumination light of visible light as a light source of illumination light, a controller 23 that controls the endoscopic system 3 as a whole, an input section 24 such as a keyboard or a touch panel, a display section 25 that displays surgery information including imaged surgery conditions, and a the water-supply water discharge section 26 that supplies a perfusion including physiological saline tea surroundings of a talus 61 of a site to be treated 100 or drains or perfuses the perfusion.

The the water-supply water-discharge section 26 circulates a perfusion at a fixed flow rate by supplying perfusion including physiological saline to surroundings including the joint of the site to be treated 100 through the arthroscope 21 or draining the perfusion. In the present embodiment, the the water-supply water-discharge section 26 is configured to supply the perfusion to the site to be treated or drain the perfusion, but the perfusion may also be supplied or drained from the ultrasonic treatment tool 2.

Figure 2:
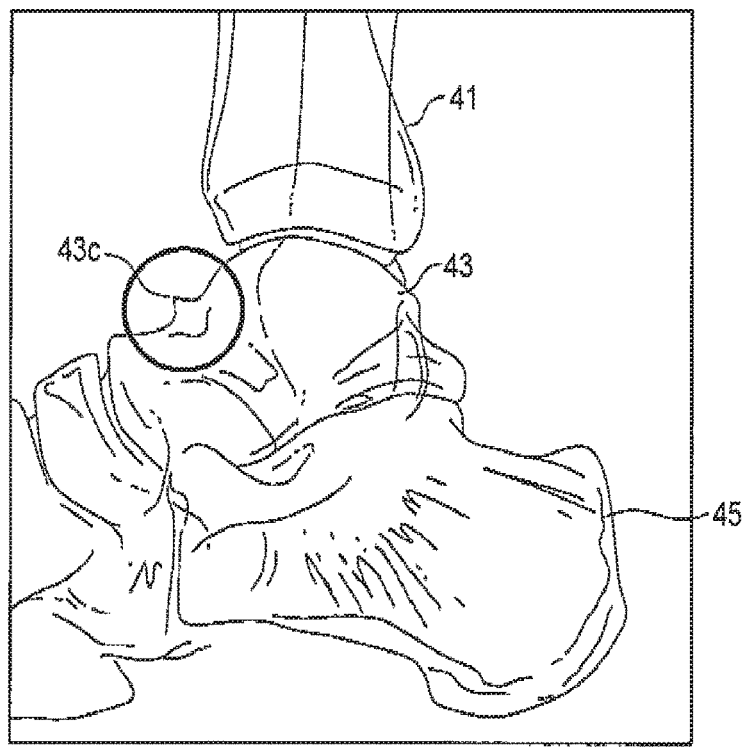
FIG. 2 is a diagram showing a location where an anterior impingement of ankle is formed.
Figure 3:
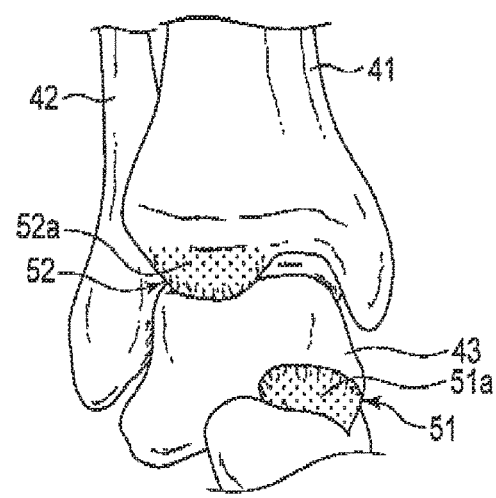
FIG. 3 is a diagram showing locations where an osteophyte is formed when viewed from the front.
Figure 4A:
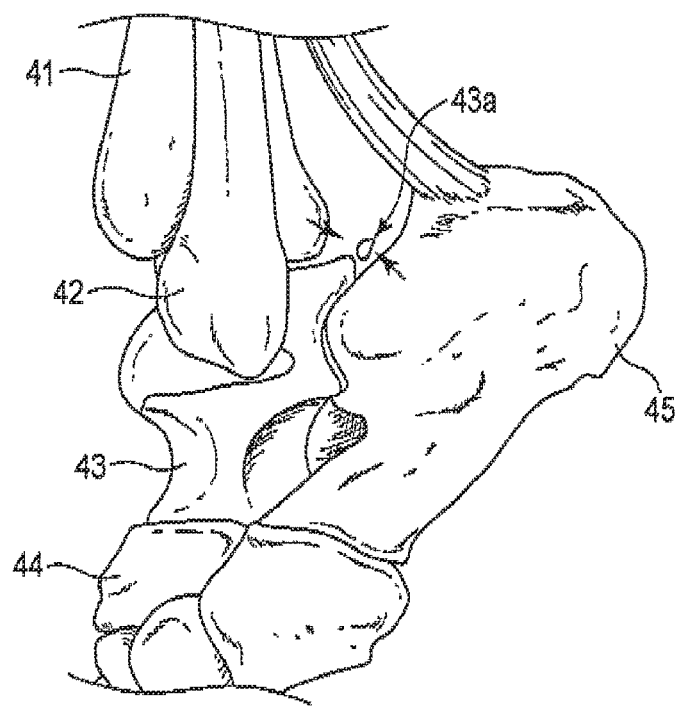
FIG. 4A is a diagram showing impairment of a lateral tubercle of posterior process of talus.
Figure 4B:
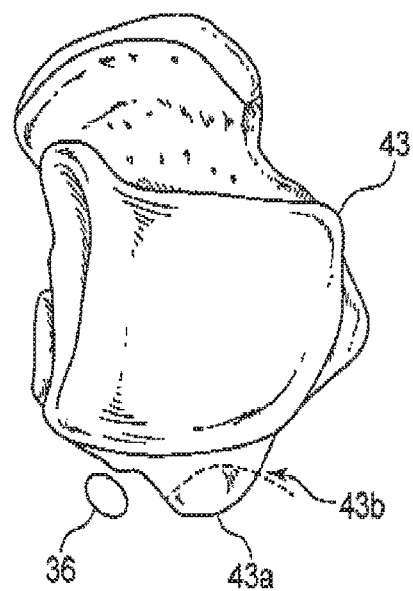
FIG. 4B is a diagram showing the lateral tubercle of posterior process of talus.
Figure 5:
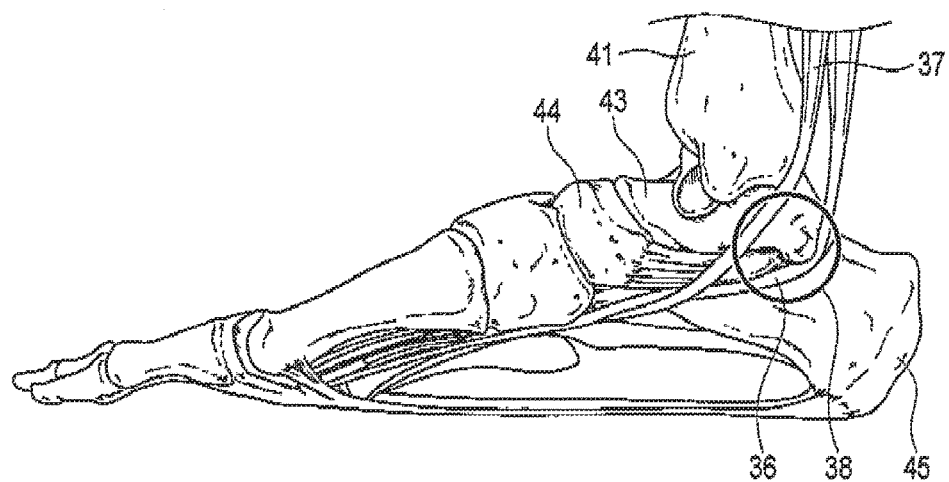
FIG. 5 is a diagram illustrating tendon sheath impairment of flexor hallucis longus muscle tendon.

FIG. 2 is a diagram showing a location where an anterior impingement of ankle is formed; FIG. 3 is a diagram showing locations where an osteophyte is formed when viewed from the front, FIG. 4A is a diagram showing lateral tubercle impairment of posterior process of talus, and FIG. 4B is a diagram showing a lateral tubercle of posterior process of talus. FIG. 5 is a diagram illustrating tendon sheath impairment of flexor hallucis longus muscle tendon.

The anterior impingement of ankle is considered to be more likely to occur in ball games in which a ball is kicked like football or competitions with outer instability in which a sprain is more likely to occur due to irregular foot motion like basketball. The ankle impingement is considered to be more likely to occur when standing up on tiptoes like in ballet or the like and in competitions in which motion (planter flexion) of stretching the instep for shooting the like is frequent like football. In both cases, pain is felt in ankles when bones hit against each other and broken or tissues or the like are put between bones.

Figure 8:
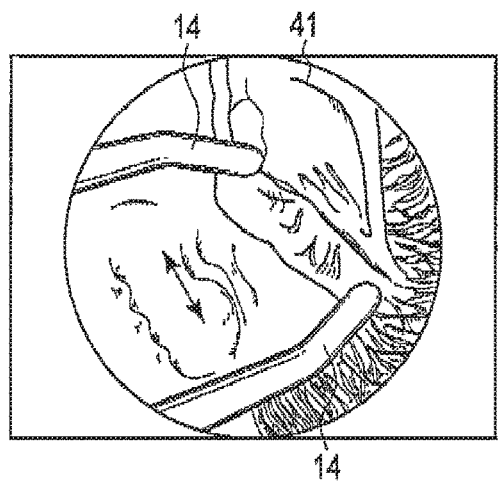
FIG. 8 is a diagram showing a state of FHL whose strangulation is canceled.

As illustrated in FIG. 2, the anterior impingement of ankle is formed as an osteophyte 43c by a repair mechanism of the articular cartilage after the lower end face of a tibia 41 and a talus 43 collide. Also, as illustrated in FIG. 3, locations where an osteophyte is likely to be formed include a lower end front of tibia 52 where an osteophyte 52a is likely to be formed on the outer side of the foot and a neck of talus 51 where an osteophyte 51a is likely to be formed on the inner side thereof. FIG. 4B shows a lateral tubercle of posterior process of talus (a so-called triangular bone) 43b in the talus 43 in a normal state. Impairment in which a triangular ossicle 43a on the side from a broken line of the lateral tubercle of posterior process of talus 43b is segmented is known. If the instep is stretched like standing up on tiptoes in ballet when the triangular ossicle 43a is positioned as illustrated in FIG. 4A, the gap between the tibia 41 and a calcaneal bone 45 becomes narrower and the triangular ossicle 43a is put therebetween, causing pain in the triangular ossicle 43a. Also if, as illustrated in FIG. 8, the tip of the lateral tubercle of posterior process protrudes, that is, the triangular bone protrudes, pain is caused when the instep is stretched. The triangular bone impairment could cause inflammation of a flexor hallucis longus muscle tendon (FHL) 36 running between inner and outer tubercles 38 illustrated in FIGS. 4B and 5.

Next, the arthroscopic surgery method for anterior impingement of ankle according to the present embodiment will be described with reference to FIGS. 2 to 8.

The method in the present embodiment is an arthroscopic surgery method for ankle impingement using an ultrasonic treatment tool roughly for a procedure for removing synovial membrane/soft tissues and securing the field of view, a procedure for removing a pathologic soft tissue of anterior impingement, and a procedure for removing osteophytes of the tibia and the talus.

Treatment tools used conventionally include a shaver that excises soft tissues, a bar ablator that shaves bones, and an ablator that performs ablation hemostasis of soft tissues. These treatment tools cut a target site by having a rotary blade and rotating the rotary blade or having a cutter blade and reciprocating the cutter blade. A site caught in the rotary blade or the cutter blade is cut.

Figure 6:
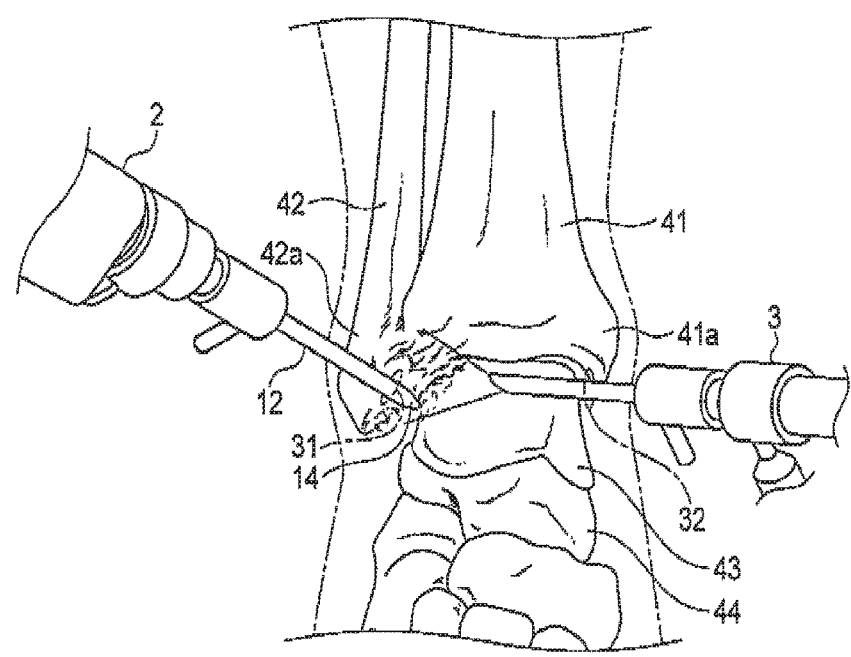
FIG. 6 is a diagram showing a surgical step of inserting a joint and an ultrasonic treatment tool into each of portals created on an anterolateral side and an anteromedial side.
Figure 7:
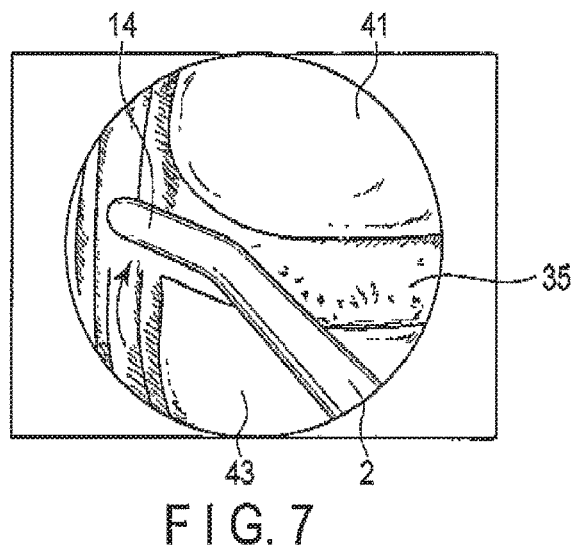
FIG. 7 is a diagram showing a surgical step of securing a field of view by removing a synovial membrane.
Figure 9:
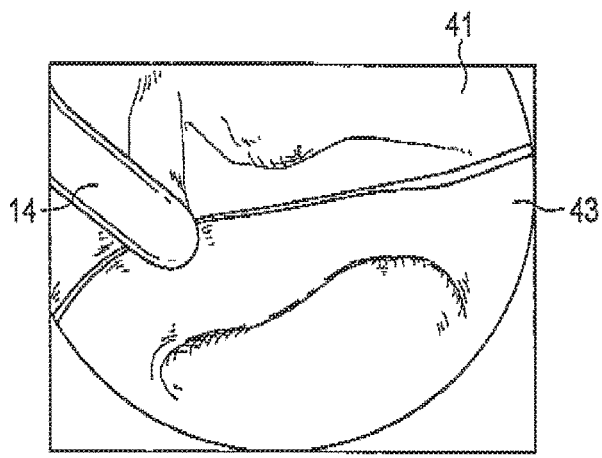
FIG. 9 is a diagram showing a surgical step of shaving off a pathologic soft tissue of anterior impingement.
Figure 10:
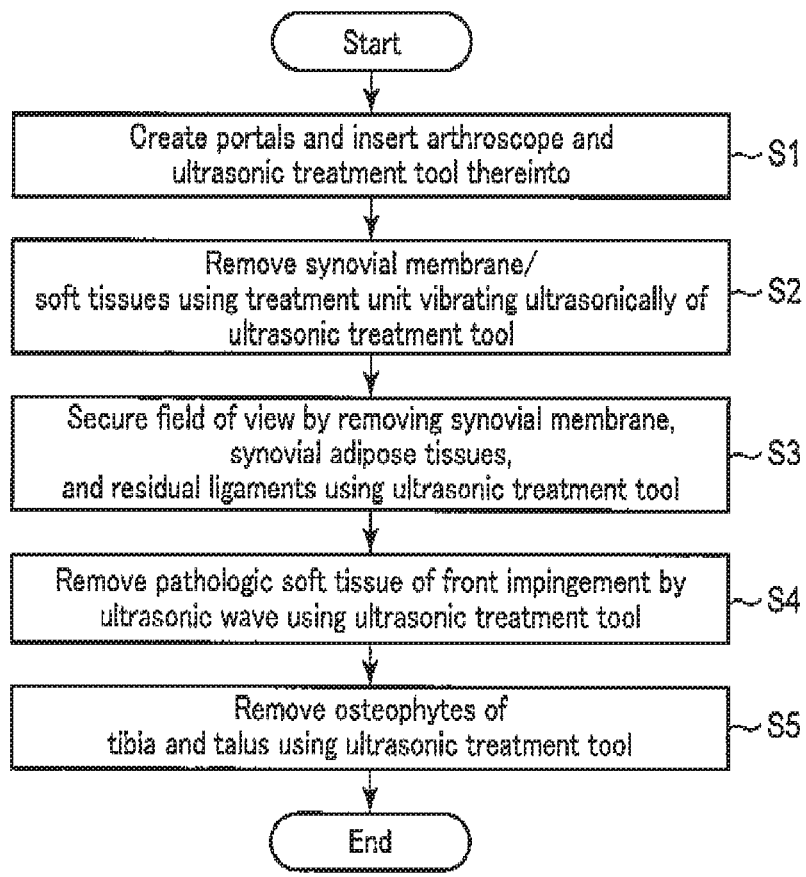
FIG. 10 is a flow chart illustrating a surgical step of arthroscopic surgery method for ankle anterior impingement.

FIG. 6 is a diagram showing a surgical step of inserting a joint and an ultrasonic treatment tool into each of portals created on an anterolateral side and anteromedial side, FIG. 7 is a diagram showing a surgical step of securing a field of view for removing a residual ligament by removing a synovial membrane, and FIG. 8 is a diagram showing a surgical step of shaving off a pathologic soft tissue of anterior impingement. FIG. 9 is a diagram showing a surgical step of removing osteophytes of a tibia and a talus. FIG. 10 is a flow chart illustrating a surgical step of an arthroscopic surgery method for ankle anterior impingement;

First, as illustrated in FIG. 6, portals 31, 32 are formed on an anteromedial side and an anterolateral side respectively as a front side of a foot. These portals cannot be formed in any position and are restricted by blood vessels and ligaments around the ankle and thus are formed approximately in positions restricted in advance. In this example, the ultrasonic treatment tool 2 is inserted from the portal 31 and the arthroscope 21 is inserted from the portal 32 (step S1).

In the procedure for removing synovial membrane/soft tissues, as illustrated in FIG. 7, the treatment section of the probe 12 of the ultrasonic treatment tool 2 is caused to vibrate ultrasonically to cut and remove synovial membranes and soft tissues of the tibia 41 and the talus 43 (step S2). Further, to secure the field of view, synovial adipose tissues and residual ligaments determined to be excess are removed and removed tissue fragments and ligament fragments are sucked and eliminated (step S3). If an osteochondritis dissecans (OCD) lesion is present in an articular cartilage of talus, the lesion is treated at the same time. These procedures can be performed to remove even surroundings in which the site to be treated is very close to nerves or blood vessels by using an ultrasonic treatment tool. It is also possible to access backward from the front portal for excision. Compared with a conventional treatment tool using a rotary blade, the probe 12 of the ultrasonic treatment tool 2 does not have a rotation transmission site and thus, as illustrated in FIG. 6, can be formed as an elongated bar of about 2 to 4 mm in diameter. The treatment section 14 at the tip of the probe 12 is not always provided linearly and can be configured to be, as illustrated it FIG. 8, curved or bent and thus, even when accessing backward from the front portal, the object to be treated can be reached and excised. In addition, the probe 12 itself can be curved to certain degree.

Next, as illustrated in FIG. 8, in the procedure for removing a pathologic soft tissue of anterior impingement, a pathologic soft tissue formed on the talus 43 as illustrated in FIG. 2 is excised using the treatment section 14 of the probe 12 vibrating ultrasonically and evidement is performed (step S4). By performing the procedure using, instead of a conventional shaver, the ultrasonic treatment tool 2, even if a pathologic soft tissue is present in an anterior joint capsule, the tissue can be excised without damaging a dorsal artery/vein of foot and deep peroneal nerves.

In addition, as illustrated in FIG. 9, osteophytes 43c, 51a, 52a of the tibia 41 and the talus 43 are removed using the treatment section 14 of the probe 12 vibrating ultrasonically (step S5). By using the ultrasonic treatment tool 2, thermal invasiveness risks to the articular surface of the talus 43 and the articular cartilage of the tibia 41 and damage risks to blood vessels/nerves are greatly reduced. In an excision procedure of osteophytes of the talus and the tibia, a conventional treatment tool has a problem of possible damage to the articular cartilage and also possible damage to blood vessels/nerves, which makes the use thereof very difficult and the utmost care needs to be taken. Particularly, an ultrasonic wave is used for cutting and thus, only osteophytes can be excised while leaving normal tissues behind.

Next, the arthroscopic surgery method for posterior impingement of ankle according to the present embodiment will be described with reference to FIGS. 4A, 4B, and 11 to 14. In surgical steps of the arthroscopic surgery method for posterior impingement of ankle, the same step reference signs are attached to steps equal to surgical steps in the aforementioned arthroscopic surgery method for anterior impingement of ankle and a detailed description thereof is omitted.

The method in the present embodiment is an arthroscopic surgery method for ankle impingement using an ultrasonic treatment tool for a procedure for removing synovial membrane/soft tissues and securing the field of view, a procedure for excising the lateral tubercle of posterior process of talus, and a procedure for dissecting the tendon sheath of flexor hallucis longus muscle tendon and canceling the strangulation.

Figure 11:
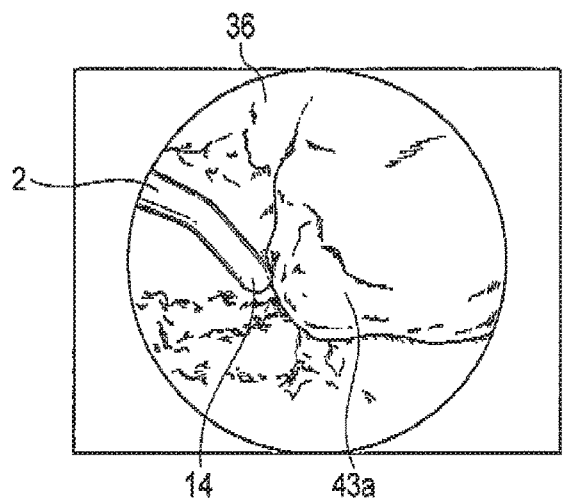
FIG. 11 is a diagram showing a surgical step of ablating and excising surroundings of the lateral tubercle of posterior process of talus.
Figure 12:
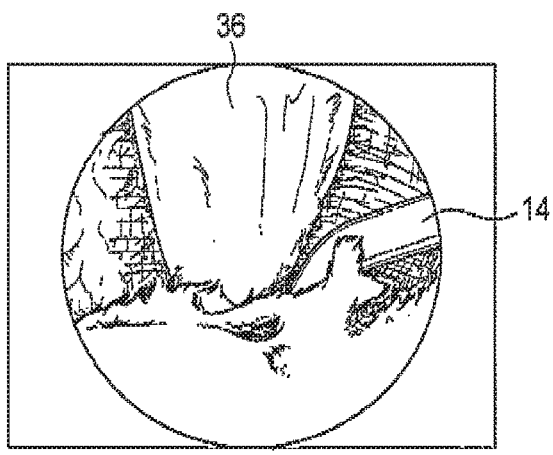
FIG. 12 is a diagram showing a surgical step of dissecting the tendon sheath of flexor hallucis longus muscle tendon (FHL) and canceling the strangulation.
Figure 13:
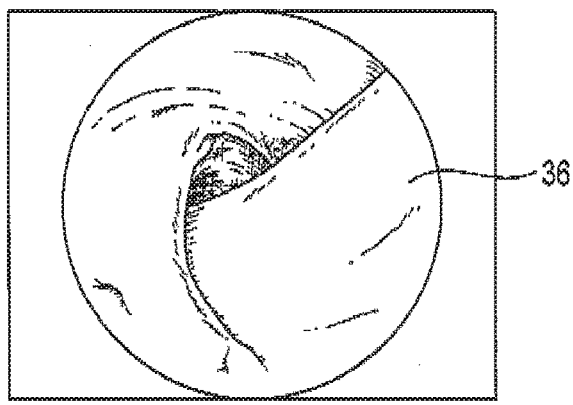
FIG. 13 is a diagram showing a surgical step of removing osteophytes of a tibia and a talus.
Figure 14:
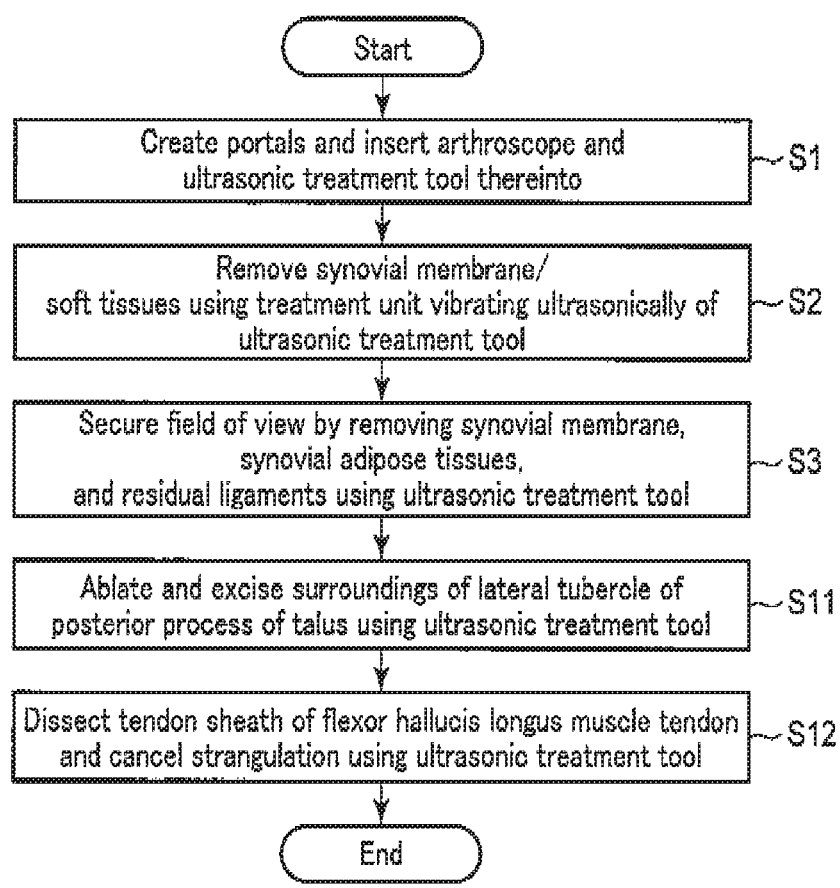
FIG. 14 is a flow chart illustrating a surgical step of an arthroscopic surgery method for posterior impingement of ankle.

FIG. 11 is a diagram showing a surgical step of ablating and excising surroundings of the lateral tubercle of posterior process of talus, FIG. 12 is a diagram showing a surgical step of dissecting the tendon sheath of flexor hallucis longus muscle tendon (FHL) and canceling the strangulation, and FIG. 13 is a diagram showing a state of FHL whose strangulation is canceled. FIG. 14 is a flow chart illustrating a surgical step of an arthroscopic surgery method for posterior impingement of ankle.

First, the ultrasonic treatment tool 2 and the arthroscope 21 are inserted into the portals 31, 32 on the anteromedial side and the anterolateral side respectively in a rear direction of the foot, that is, on a heel side (step S1) and synovial membranes and soft tissues of the tibia 41 and the talus 43 are cut and removed by the treatment section 14 of the probe 12 vibrating ultrasonically (step S2). Further, to secure the field of view, tissue fragments and ligament fragments are removed and sucked for elimination (step S3). If an osteochondritis dissecans (OCD) lesion is present in an articular cartilage of talus, the lesion is treated at the same time.

Next, in the procedure for ablating and excising surroundings of the lateral tubercle of posterior process of talus as illustrated in FIG. 11, the triangular bone 43a is easily dissected and separated by the treatment section 14 of the probe 12 vibrating ultrasonically (step S11).

The treatment section provided at the tip of the probe in the present embodiment cuts the bone like crushing even if the bone is a very hard lateral tubercle of posterior process of talus without fracture by mechanical cutting (so-called hammering effect or hammering action) that crushes by knocking using ultrasonic vibrations and shaves off. In the present embodiment, compared with a treatment time when a conventional small joint bar is used, the speed of dissection is fast and the treatment time can be reduced so that the load on the patient can be reduced. Also even in the neighborhood of the flexor hallucis longus muscle tendon, the lateral tubercle of posterior process of talus can safely be excised with respect to surroundings thereof. Further, the object to be treated can be excised by accessing backward from the front portal.

Next as illustrated in FIGS. 12 and 13, the tendon sheath of the flexor hallucis longus muscle tendon 36 is dissected and also the strangulation is canceled using the treatment section 14 vibrating ultrasonically of the ultrasonic treatment tool 2 (step S12).

In these procedures, even if the treatment section vibrating infinitesimally comes into contact with a site other than the site to the treated for a short period of time, no serious damage will be done to the side. Thus, even in conditions in which nerves or blood vessels around the site to be treated are very close, the site can be removed easily. The probe is not always provided linearly with respect to the treatment section at the tip thereof and can be configured to be curved or bent and thus, even when accessing backward from the front portal, the object to be treated can be reached and excised.

Incidentally, the arthroscopic surgery method for anterior impingement of ankle and the arthroscopic surgery method for posterior impingement of ankle can successively be performed. In such a case, the arthroscope and the ultrasonic treatment tool inserted into the rear portal on the heel side for the previous treatment are once taken out of the rear portal and then the arthroscope and the ultrasonic treatment tool are inserted into the front portal on the opposite side. After the tendon sheath is dissected and the strangulation is canceled in step S12 of the arthroscopic surgery method for posterior impingement of ankle, the pathologic soft tissue on the talus 43 is excised and evidement is performed in steps S4, S5 of the arthroscopic surgery method for anterior impingement of ankle and then, the osteophytes 43c, 51a, 52a of the tibia 41 and the talus 43 are excised.

The ultrasonic treatment tool according to the present embodiment has, as described above, the following operation/working effects:

Firstly, the ultrasonic treatment tool can be made narrow or thin in thickness and is not limited to a linear probe structure and so, with its excellent accessibility, can easily treat a site unreachable by an existing treatment tool.

Secondly, ultrasonic vibrations are used for shaving and therefore, the cut surface can be made smooth and postoperative conditions are good and further, ultrasonic vibrations are used for shaving and therefore, thermal damage to the site to be treated can be reduced, postoperative conditions are good, and minimal invasiveness is superior.

Thirdly, the ultrasonic treatment tool can treat both of soft tissues and hard tissues and therefore, replacement work of treatment tools can be reduced and burdens on technicians can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An arthroscopic surgery method for ankle impingement comprising:
   inserting an ultrasonic treatment tool into a portal formed in a position specified in advance such that a tip of a probe of the ultrasonic treatment tool reaches a posterior process of a talus and a tendon sheath of a flexor hallucis longus muscle tendon to be treated;
   removing the posterior process of the talus using the tip of the probe that is vibrating ultrasonically to knock the posterior process of the talus and pulverize the posterior process of the talus into extremely fine pieces; and
   excising a fibrous tendon sheath of the tendon sheath of the flexor hallucis longus muscle tendon and canceling strangulation of the tendon sheath of the flexor hallucis longus muscle tendon by shaving the posterior process of the talus using an ultrasonic vibration of the ultrasonic treatment tool.

2. The arthroscopic surgery method for ankle impingement according to claim 1, wherein the portal is a rear portal.

3. The arthroscopic surgery method for ankle impingement according to claim 1, wherein the portal is a front portal.

4. The arthroscopic surgery method for ankle impingement according to claim 1, wherein
   the portal forms a front portal and a rear portal and
   when the portal is the front portal, the method for the front portal is subsequently performed after the rear portal.

5. An arthroscopic surgery method for ankle impingement comprising:
   positioning an ultrasonic treatment tool such that a tip of a probe of the ultrasonic treatment tool reaches an osteophyte on an inner side of a talus and/or a tibia;
   shaving a synovial membrane using the probe vibrating ultrasonically; and
   removing an osteophyte using the tip of the probe that is vibrating ultrasonically to knock the osteophyte and pulverize the osteophyte into extremely fine pieces.

6. The arthroscopic surgery method for ankle impingement according to claim 5, wherein the osteophyte is an osteophyte of a lower end front of the tibia and an osteophyte of a neck of the talus.

7. An arthroscopic surgery method for ankle impingement performed under an arthroscope comprising:
   a first surgical step of inserting an ultrasonic treatment tool and the arthroscope into a joint fissure between a talus and a tibia through at least two portals;
   a second surgical step of circulating a perfusion around a location to be treated;
   a third surgical step of removing a synovial membrane/soft tissue;
   a fourth surgical step of securing a field of view by cutting and eliminating a tissue and a ligament determined to be excess;
   a fifth surgical step of excising a lateral tubercle of a posterior process of the talus;
   a sixth surgical step of dissecting a tendon sheath of a flexor hallucis longus muscle tendon and canceling strangulation;
   a seventh surgical step of removing a pathologic soft tissue of anterior impingement; and
   an eighth surgical step of removing an osteophyte of the tibia and the talus, wherein
   a probe of the ultrasonic treatment tool that is vibrating ultrasonically is used for each procedure of at least the third surgical step to the eighth surgical step, and
   in the eighth surgical step, the osteophyte of the tibia and the talus is knocked and pulverized by a tip of the probe into extremely fine pieces to remove the osteophyte of the tibia and the talus.

8. The arthroscopic surgery method for ankle impingement according to claim 7, wherein
   nerves, blood vessels, and ligaments present close to and around the location to be treated are not damaged while performing the third through eighth surgical steps.

* * * * *